United States Patent
Yeh (10) Patent No.: US 11,730,353 B2
(45) Date of Patent: Aug. 22, 2023

(54) AMBIENT LIGHT OTOSCOPE

(71) Applicant: Forrest Yeh, Piedmont, CA (US)

(72) Inventor: Forrest Yeh, Piedmont, CA (US)

(*) Notice: Subject to any disclaimer, the term of this patent is extended or adjusted under 35 U.S.C. 154(b) by 321 days.

(21) Appl. No.: 17/083,130

(22) Filed: Oct. 28, 2020

(65) Prior Publication Data

US 2022/0125292 A1    Apr. 28, 2022

(51) Int. Cl.
*A61B 1/227* (2006.01)
*A61B 1/00* (2006.01)

(52) U.S. Cl.
CPC .......... *A61B 1/227* (2013.01); *A61B 1/00165* (2013.01); *A61B 1/00195* (2013.01)

(58) Field of Classification Search
CPC ............................. A61B 1/227; A61B 1/00165
USPC ................................................ 600/201–245
See application file for complete search history.

(56) References Cited

U.S. PATENT DOCUMENTS

| | | | | |
|---|---|---|---|---|
| 4,380,998 A | * | 4/1983 | Kieffer, III | G01J 5/028 374/E1.013 |
| 5,588,952 A | * | 12/1996 | Dandolu | A61B 90/30 604/27 |
| 2017/0027448 A1 | * | 2/2017 | Carr | A61B 1/0646 |

* cited by examiner

*Primary Examiner* — Eduardo C Robert
*Assistant Examiner* — Tara Rose E Carter (57) ABSTRACT

An otoscope that utilizes ambient light is disclosed. The otoscope includes a fiberoptic cable(s), as opposed to batteries, to illuminate the inspection area. The otoscope made of non-metallic and/or non-ferrous materials to permit its safe use in highly flammable oxygen or magnetic environments. The otoscope includes a handle, a head coupled to the handle, and a specula coupled to the head. An eye piece coupled to the head opposite the specula. A reflective lens is positioned within the head. A fiber optic cable is positioned within the handle. The handle includes a first end positioned opposite a second end. The head is coupled to the first end. The fiber optic cable provides light to the reflective lens. The fiber optic cable extends from the front end to the second end. The reflective lens is oriented to reflect light to the specula.

20 Claims, 11 Drawing Sheets

AMBIENT LIGHT OTOSCOPE

FIELD OF THE INVENTION

The present disclosure relates generally to otoscope. More specifically, the present disclosure describes ambient light otoscope.

BACKGROUND OF THE INVENTION

An otoscope is a medical device used for observing various pathologies in human orifices (e.g., head, eyes, ears, nose, throat) during physical exams. For example, otoscopes can be used to screen an ear for tympanic membrane ruptures, inflammation, infections, discharge, obstructions, and tympanometry. The eyes can be screened for pupillary light reactivity and the nose can also be screened for mucous membrane characteristics, sepal deviations, inflammation, and polyp presence. Otoscopes can be used to screen the mouth for tonsillar characteristics, oral thrush, deviations, obstructions, neoplasms, infections, inflammation, and ulcerations. Otoscopes have been an essential part of the physician's toolkit for almost 100 years and currently require batteries and illuminating bulbs for operation.

In settings of high oxygen pressures (e.g., hyperbaric chambers) and metal device restrictions (e.g., MRI), devices that require batteries, such as traditional otoscopes, cannot be safely used. For examples, the restriction on the use of battery powered instruments poses a particular problem with hyperbaric oxygen therapy, which can induce middle ear barotrauma that cannot be easily observed without an otoscope. Hence, there exists a need in the art for non-battery powered otoscope

BRIEF DESCRIPTION OF THE DRAWINGS

Some of the embodiments will be described in detail, with reference to the following figures, wherein like designations denote like members, wherein.

Unless otherwise specifically noted, articles depicted in the drawings are not necessarily drawn to scale.

DETAIL DESCRIPTIONS OF THE INVENTION

As a preliminary matter, it will readily be understood by one having ordinary skill in the relevant art that the present disclosure has broad utility and application. As should be understood, any embodiment may incorporate only one or a plurality of the above-disclosed aspects of the disclosure and may further incorporate only one or a plurality of the above-disclosed features. Furthermore, any embodiment discussed and identified as being "preferred" is considered to be part of a best mode contemplated for carrying out the embodiments of the present disclosure. Other embodiments also may be discussed for additional illustrative purposes in providing a full and enabling disclosure. Moreover, many embodiments, such as adaptations, variations, modifications, and equivalent arrangements, will be implicitly disclosed by the embodiments described herein and fall within the scope of the present disclosure.

Accordingly, while embodiments are described herein in detail in relation to one or more embodiments, it is to be understood that this disclosure is illustrative and exemplary of the present disclosure and are made merely for the purposes of providing a full and enabling disclosure. The detailed disclosure herein of one or more embodiments is not intended, nor is to be construed, to limit the scope of patent protection afforded in any claim of a patent issuing here from, which scope is to be defined by the claims and the equivalents thereof. It is not intended that the scope of patent protection be defined by reading into any claim a limitation found herein that does not explicitly appear in the claim itself.

Additionally, it is important to note that each term used herein refers to that which an ordinary artisan would understand such term to mean based on the contextual use of such term herein. To the extent that the meaning of a term used herein—as understood by the ordinary artisan based on the contextual use of such term—differs in any way from any particular dictionary definition of such term, it is intended that the meaning of the term as understood by the ordinary artisan should prevail.

Furthermore, it is important to note that, as used herein, "a" and "an" each generally denotes "at least one," but does not exclude a plurality unless the contextual use dictates otherwise. When used herein to join a list of items, "or" denotes "at least one of the items," but does not exclude a plurality of items of the list. Finally, when used herein to join a list of items, "and" denotes "all of the items of the list."

The following detailed description refers to the accompanying drawings. Wherever possible, the same reference numbers are used in the drawings and the following description to refer to the same or similar elements. While many embodiments of the disclosure may be described, modifications, adaptations, and other implementations are possible. For example, substitutions, additions, or modifications may be made to the elements illustrated in the drawings, and the methods described herein may be modified by substituting, reordering, or adding stages to the disclosed methods. Accordingly, the following detailed description does not limit the disclosure. Instead, the proper scope of the disclosure is defined by the appended claims. The present disclosure contains headers. It should be understood that these headers are used as references and are not to be construed as limiting upon the subjected matter disclosed under the header.

Other technical advantages may become readily apparent to one of ordinary skill in the art after review of the following figures and description. It should be understood at the outset that, although exemplary embodiments are illustrated in the figures and described below, the principles of the present disclosure may be implemented using any number of techniques, whether currently known or not. The present disclosure should in no way be limited to the exemplary implementations and techniques illustrated in the drawings and described below.

Unless otherwise indicated, the drawings are intended to be read together with the specification and are to be considered a portion of the entire written description of this invention. As used in the following description, the terms "horizontal", "vertical", "left", "right", "up", "down" and the like, as well as adjectival and adverbial derivatives thereof (e.g., "horizontally", "rightwardly", "upwardly", "radially", etc.), simply refer to the orientation of the illustrated structure as the particular drawing figure faces the reader. Similarly, the terms "inwardly," "outwardly" and "radially" generally refer to the orientation of a surface relative to its axis of elongation, or axis of rotation, as appropriate. As used herein, the term "dorsal" refers to positions that are located near, on, or towards the upper or top side of a structure.

The present disclosure includes many aspects and features. Moreover, while many aspects and features relate to, and are described in the context of an ambient light otoscope, embodiments of the present disclosure are not limited to use only in this context. The instant disclosure seeks to disclose an otoscope that utilizes ambient light and a fiberoptic cable(s), as opposed to batteries, to illuminate the inspection area. The instant disclosure also seeks to provide an otoscope that is completely composed of non-metallic and/or non-ferrous materials (i.e. plastic and/or polymer composites) to thereby permit its safe use in highly flammable oxygen (e.g., greater than 21% PPO2) and/or magnetic environments.

An otoscope is a medical device used for observing various pathologies in human orifices (e.g., head, eyes, ears, nose, throat) during physical exams. For example, otoscopes can be used to screen an ear for tympanic membrane ruptures, inflammation, infections, discharge, obstructions, and tympanometry. The eyes can be screened for pupillary light reactivity and the nose can also be screened for mucous membrane characteristics, sepal deviations, inflammation, and polyp presence. Otoscopes can be used to screen the mouth for tonsillar characteristics, oral thrush, deviations, obstructions, neoplasms, infections, inflammation, and ulcerations. Otoscopes have been an essential part of the physician's toolkit for almost 100 years and currently require batteries and illuminating bulbs or Light-Emitting Diodes (LEDs) for operation.

Figure 1:
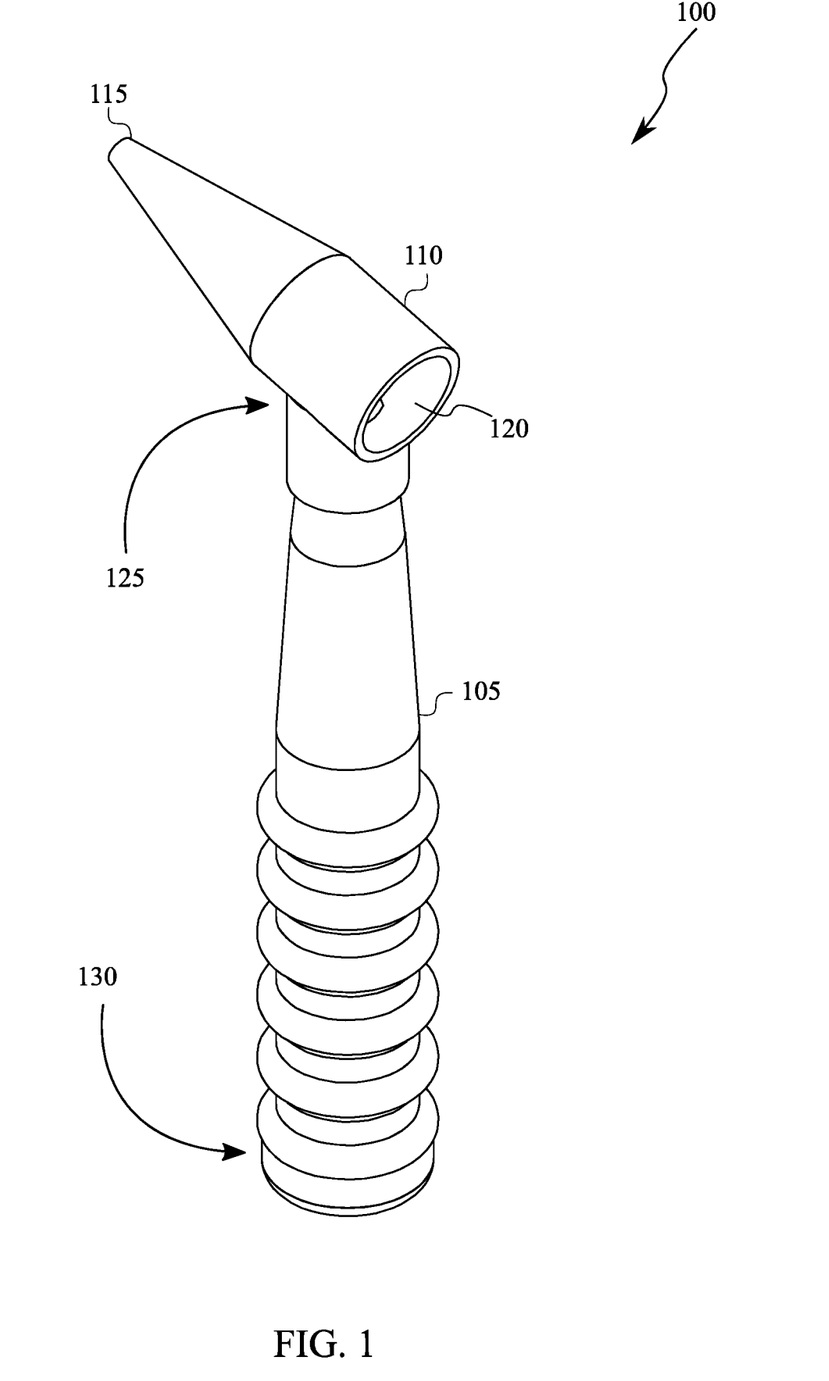
FIG. 1 depicts a top perspective view of an otoscope, according to some embodiments.
Figure 2:
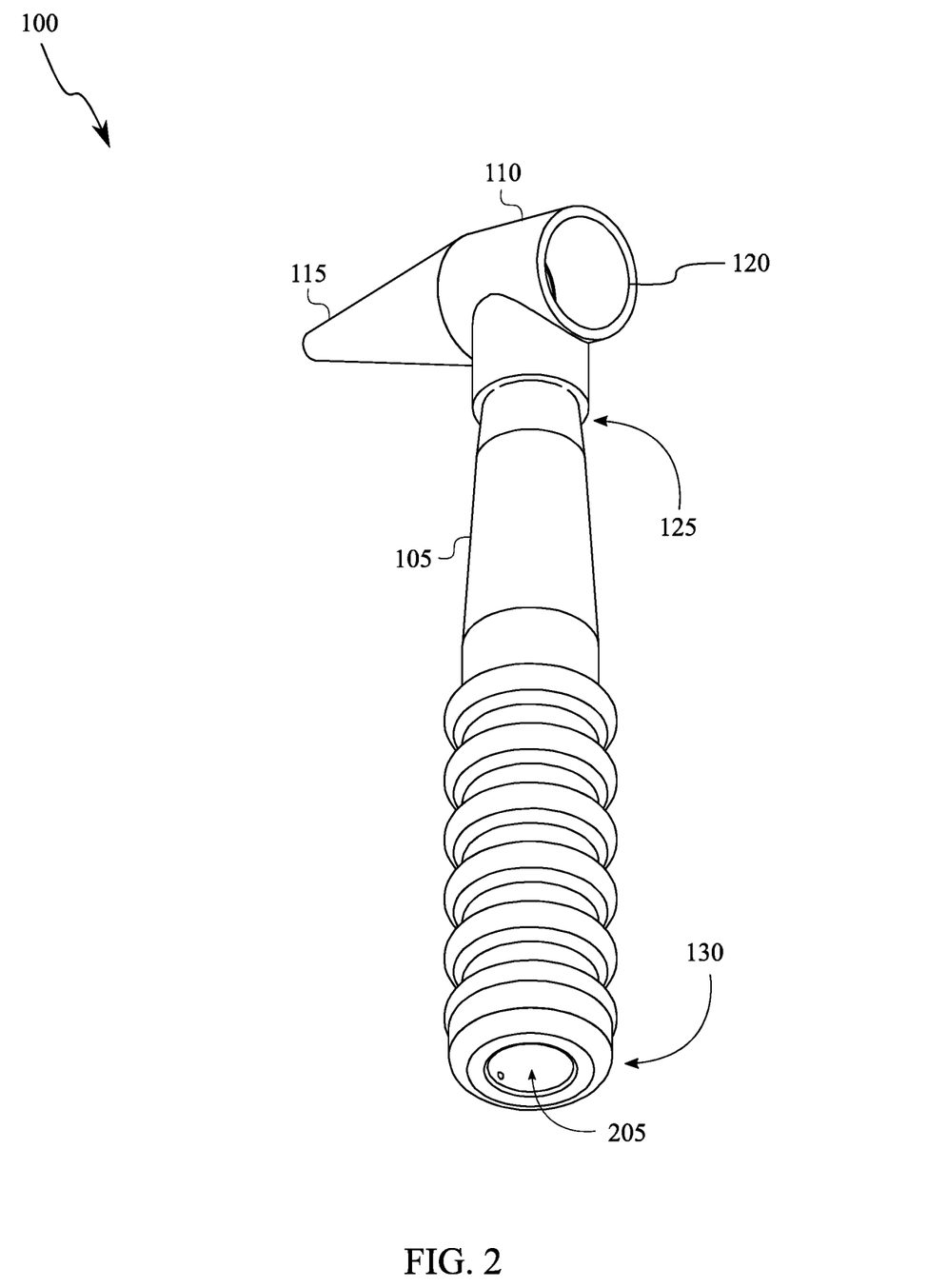
FIG. 2 depicts a bottom perspective view of the otoscope, according to other embodiments.

In settings of high oxygen pressures (e.g., hyperbaric chambers) and metal device restrictions (e.g., magnetic resonance imaging), devices that require batteries or illuminating filamentous bulbs, such as traditional otoscopes, cannot be safely used. For examples, the restriction on the use of battery powered instruments poses a particular problem with hyperbaric oxygen therapy, which can induce middle ear barotrauma that cannot be easily observed without an otoscope. Hence, there exists a need in the art for non-battery powered otoscope FIG. 1 depicts a top perspective view of an otoscope, generally 100, according to some embodiments. The otoscope 100 preferably includes a head 110, a specula 115 coupled to the head, an eye piece 120 coupled to the head 110 opposite the specula 115. The eye piece 120 is a low-power magnifying lens, typically around 8 diopters. The specula 115 can be a speculum known in the art and can have a form that is dependent on the orifice for which it is designed (e.g., head, eyes, ears, nose, throat, and similar orifices). The specula 115 allows the user to view inside a patient's body. The handle 105 comprises a first end 125 and a second end 130 positioned opposite the first end 125. The head 110 is coupled to the first end 125. FIG. 2 depicts a bottom perspective view of the otoscope, according to other embodiments. A reflective channel 205 longitudinally extends within the handle 105 from the first end 125 to the second end 130, according to certain embodiments. In other words, the reflective channel 205 longitudinally traverses the inside of the handle 105 from the first end 125 to the second end 130.

Figure 3:
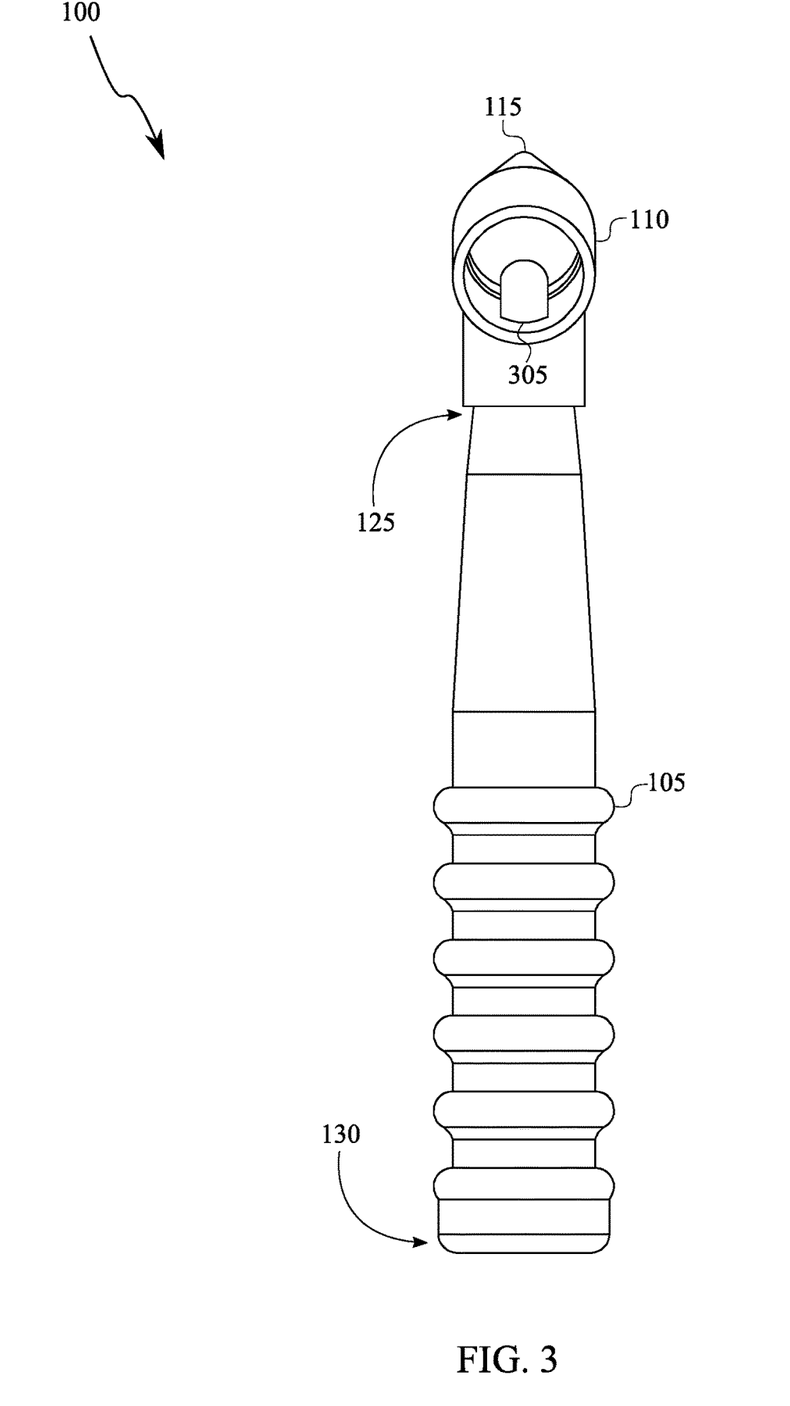
FIG. 3 depicts a rear view of the otoscope, according to certain embodiments.
Figure 4:
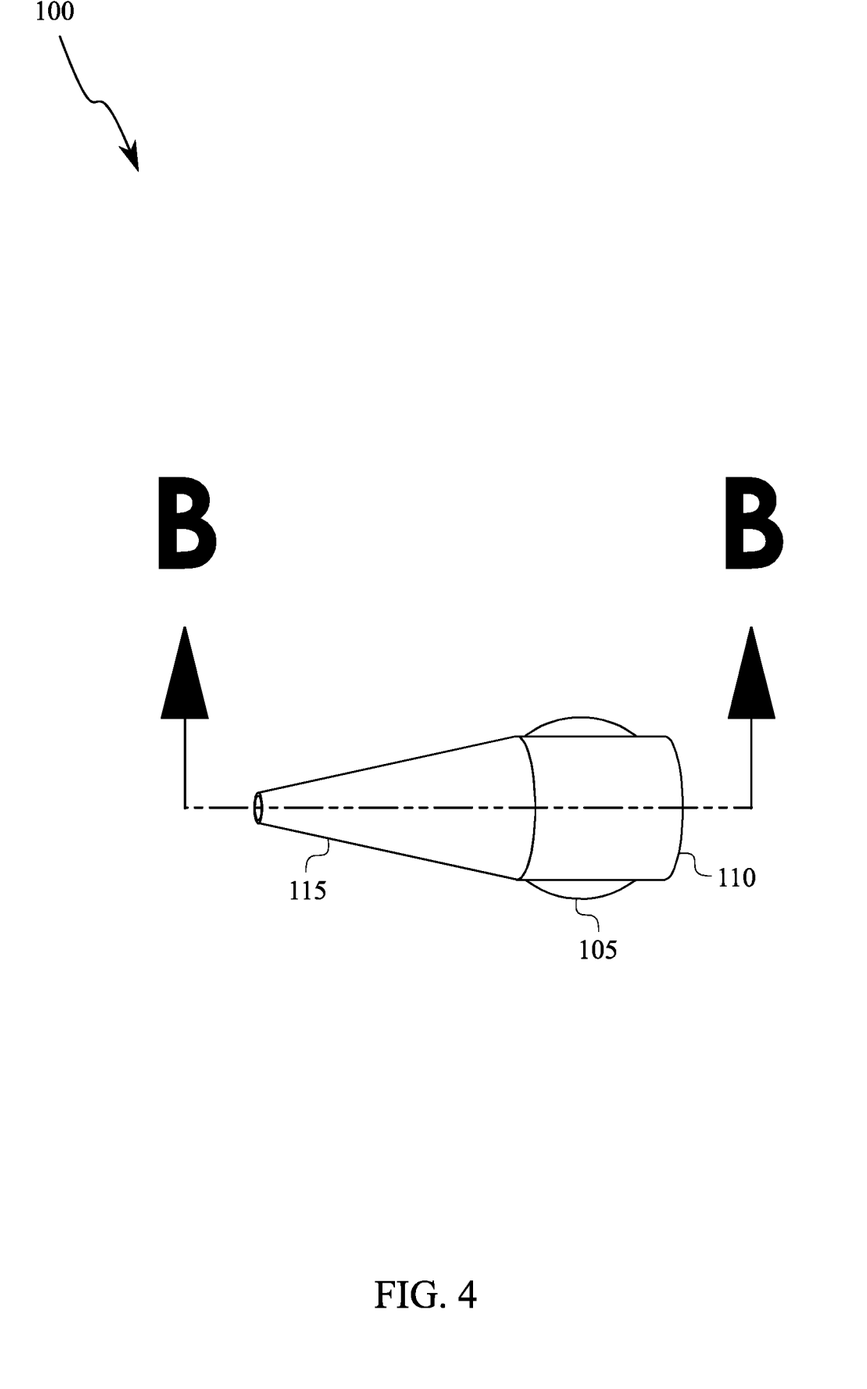
FIG. 4 depicts a top view of the otoscope, according to yet still other embodiments.
Figure 5:
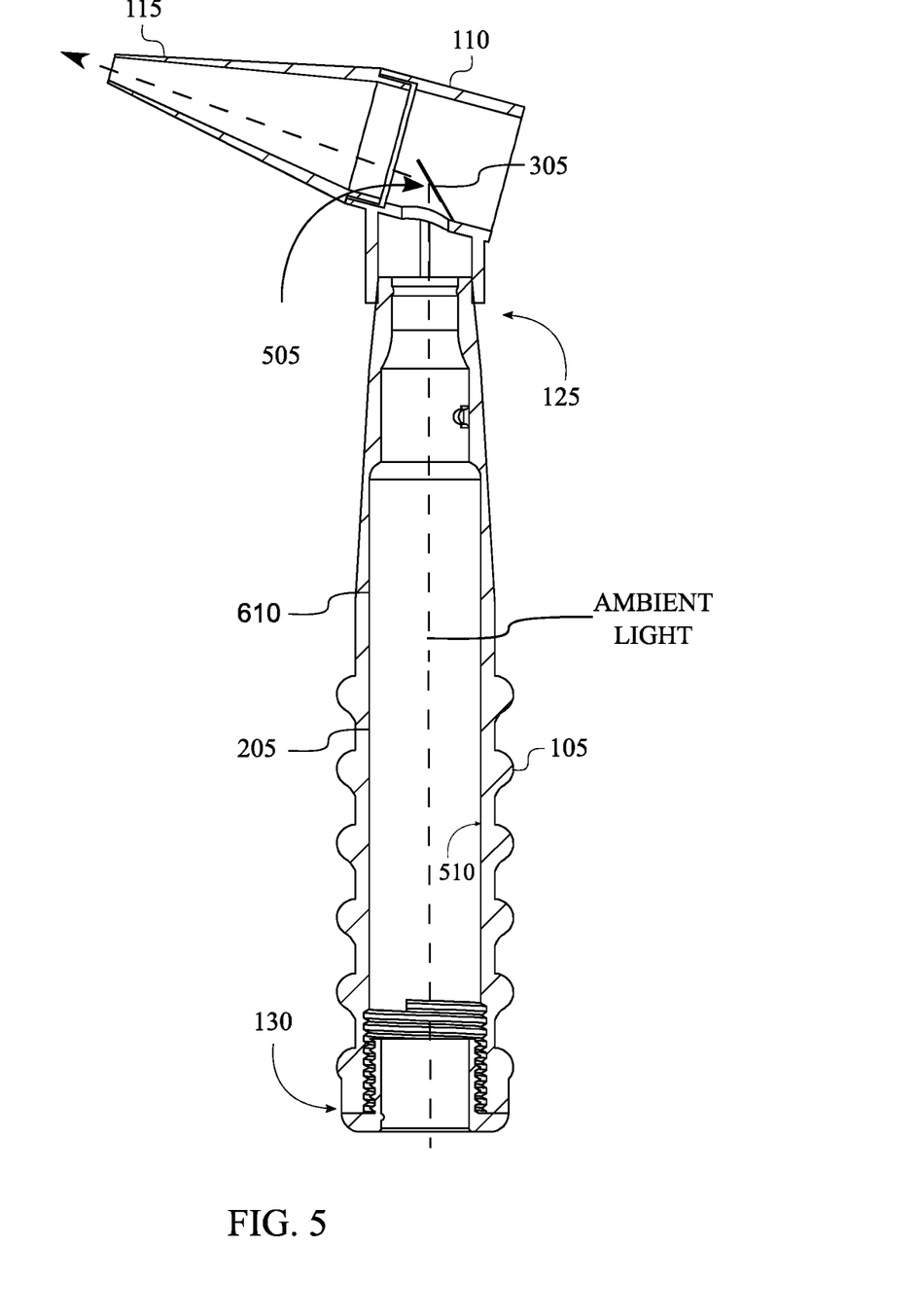
FIG. 5 depicts a cut through view of the otoscope along axis B of FIG. 4, according to some embodiments.

FIG. 3 depicts a rear view of the otoscope, according to certain embodiments. The head 110 includes a reflective lens 305 positioned therein. FIG. 4 depicts a top view of the otoscope, according to yet still other embodiments. Specifically, FIG. 4 depicts an additional view of the specula 115 relative to the head 110. FIG. 4 also depicts axis B positioned along the median axis. FIG. 5 depicts a cut through view of the otoscope along axis B of FIG. 4, according to some embodiments.

Figure 6:
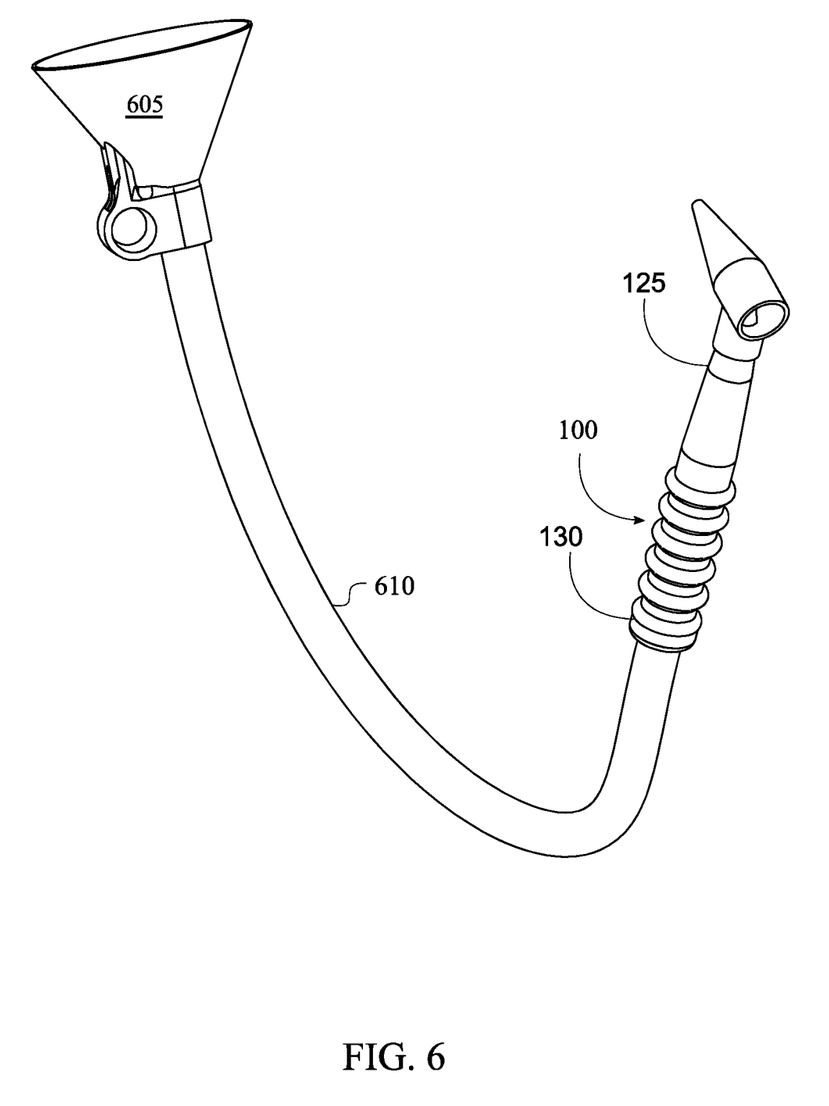
FIG. 6 depicts the otoscope coupled to a light focusing component via a fiber optic cable, according to other embodiments.
Figure 7:
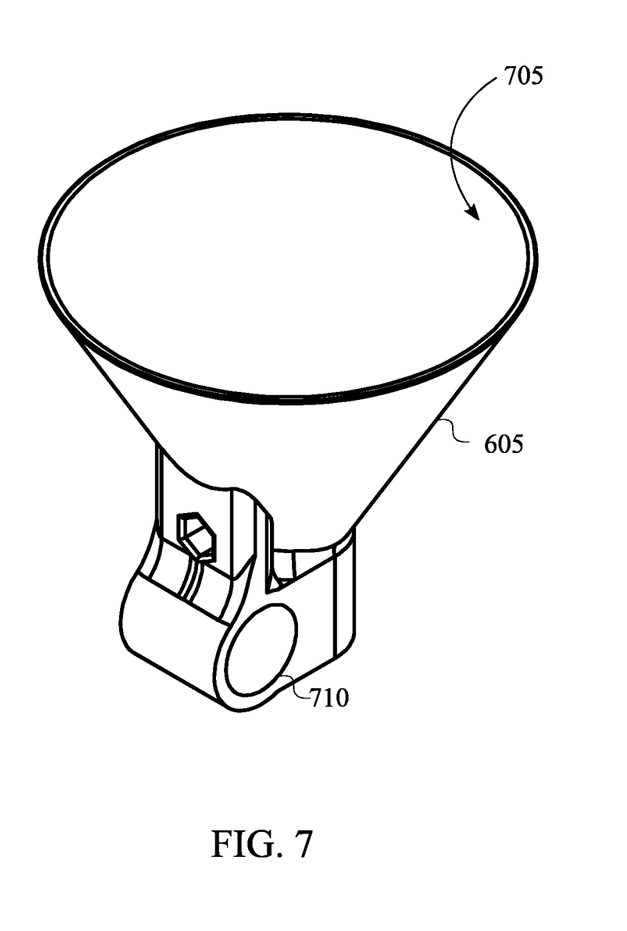
FIG. 7 depicts a top perspective view of the light focusing component, according to certain embodiments.
Figure 8:
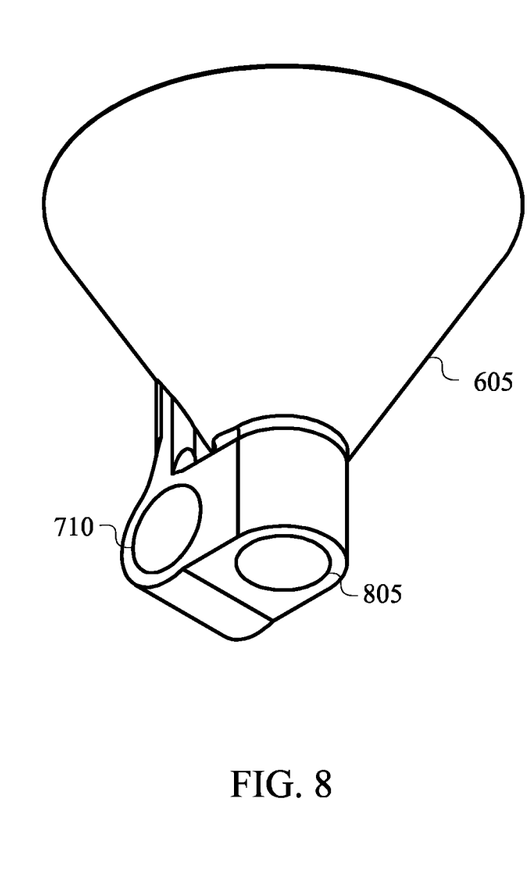
FIG. 8 depicts a bottom perspective view of the light focusing component, according to yet still other embodiments.
Figure 9:
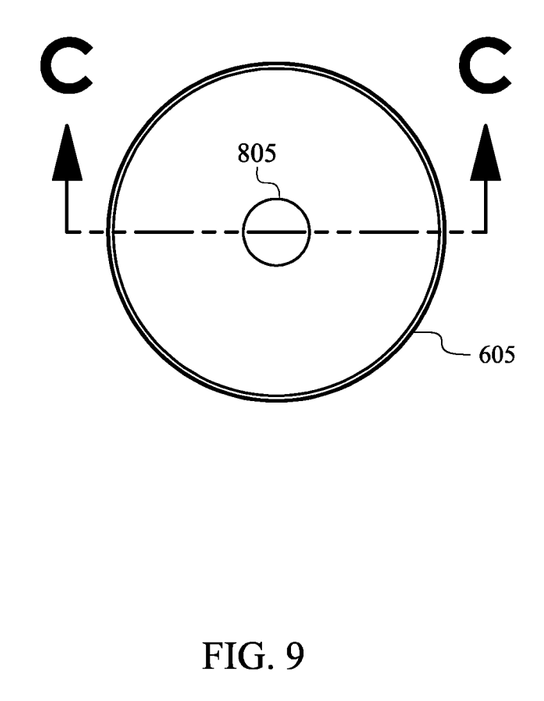
FIG. 9 depicts a top view of the perspective view of the light focusing component, according to some embodiments.
Figure 10:
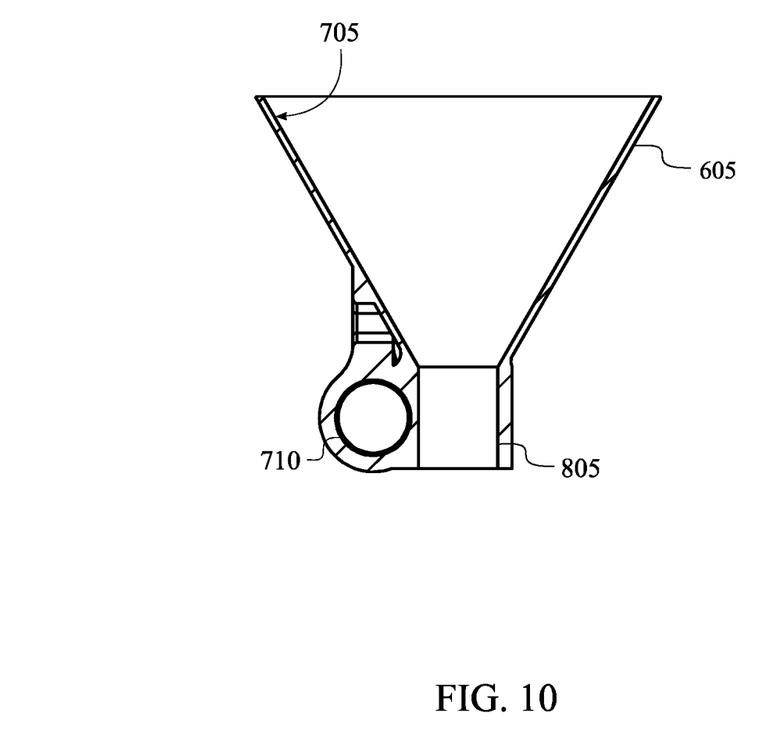
FIG. 10 depicts a cut through view of the light focusing component along axis C of FIG. 9, according to other embodiments.

The reflective channel 205 receives ambient light (e.g. from the second end 130) and reflects it to a reflective lens 305 angularly positioned within the head 110. The reflective lens 305 is oriented to reflect the ambient light to the specula 115. The otoscope 100 also includes a fiber optic cable 610 that is positioned in the handle 105, as depicted in FIG. 6. Here, the second end 130 receives the fiber optic cable 610. In other embodiments, a fiber optic cable 610 is coupled to the second end 130. In certain embodiments, the fiber optic cable 610 may extend any length into the reflective channel 205 before reaching the first end 125. The fiber optic cable 610 preferably extends from the first end 125 to the second end 130. The fiber optic cable 610 preferably provides light to the reflective lens 305.

The reflective lens 305 is oriented to reflect light to the specula 115. Compression of the head 110 may stabilize the fiber optic cable 610 within the reflective channel 205. The fiber optic cable 610 provides the ambient light to the reflective channel reflective channel 205. A light focusing component 605 is functionally coupled to the fiber optic cable 610. As depicted in FIGS. 7-10, the light focusing component 605 is preferably conically shaped to capture ambient light and channel it to the fiber optic cable 610 via a channeling orifice 805. In some embodiments, the light focusing component 605 comprises a lens to focus light. The light focusing component 605 provides (i.e. channels or funnels) ambient light to the fiber optic cable 610.

Figure 11:
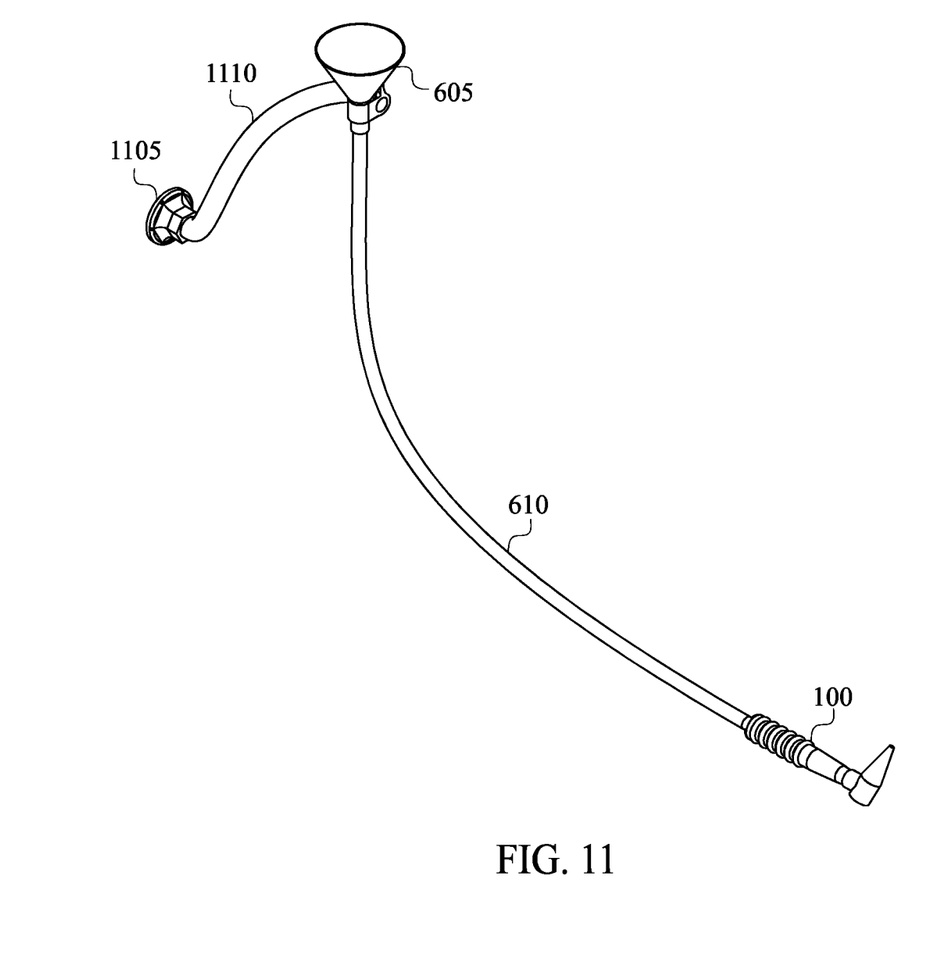
FIG. 11 depicts a hands-free version of the otoscope, according to certain embodiments.
Figure 12:
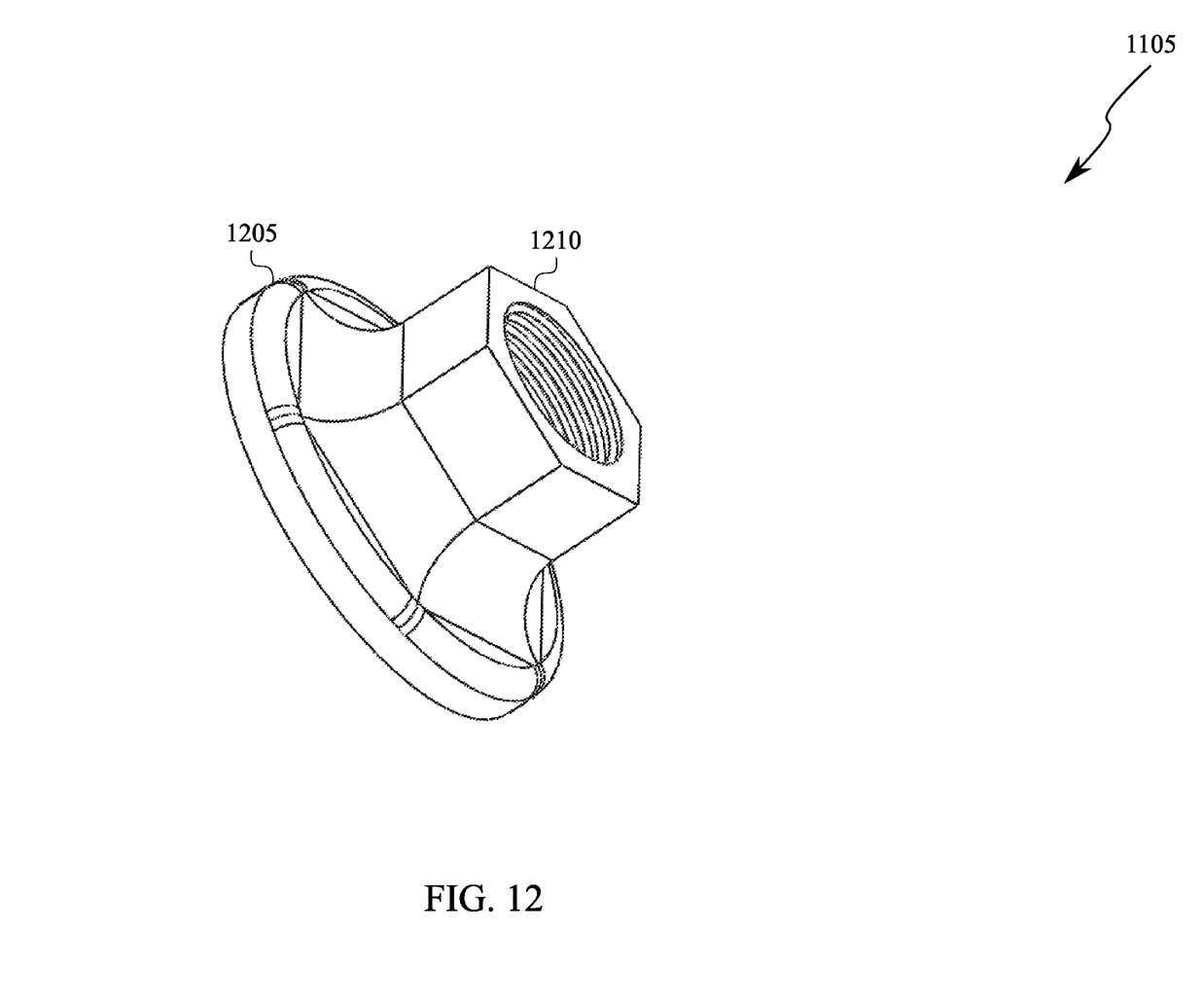
FIG. 12 depicts a front perspective view of a mount, according to yet still other embodiments.
Figure 13:
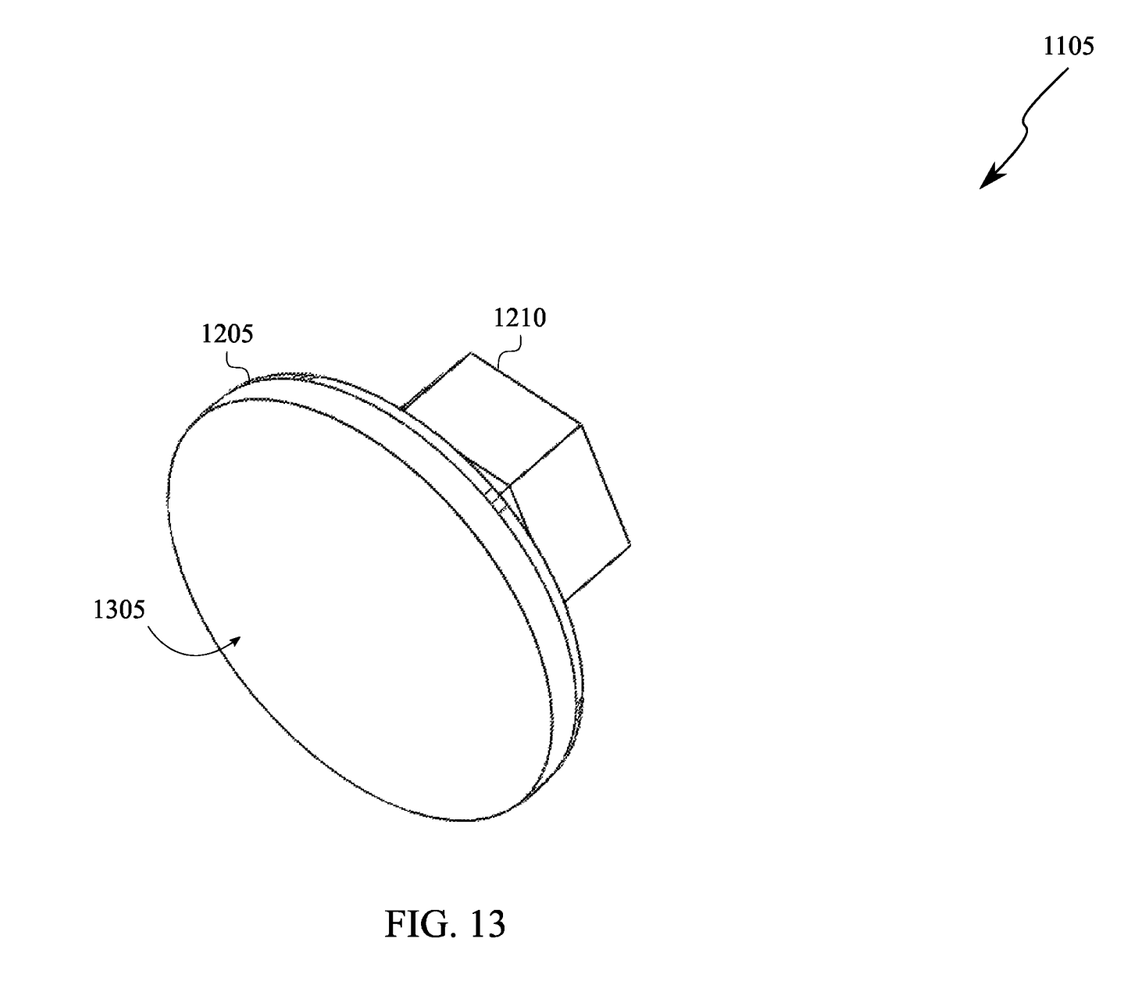
FIG. 13 depicts a perspective view of the mount, according to some embodiments.

In preferred embodiments, the light focusing component 605 includes an orienting orifice 710 that is positioned proximate to a channeling orifice 805. The channeling orifice 805 is functionally coupled to the fiber optic cable 610 and channels ambient light thereto. FIG. 11 depicts a hands-free version of the otoscope, according to certain embodiments. Although users can hold the otoscope 100 in place, the otoscope 100 preferably includes an arm 1110 that is pivotably coupled to the light focusing component 605. The arm 1110 is preferably dynamically positionable to, for example, orient the light focusing component 605 towards the ambient light. The arm 1110 can be telescoping and/or include one or more hinges. Here, a mount 1105 is coupled to the arm 1110 opposite the light focusing component 605. As depicted in FIGS. 12-13, the mount 1105 includes a base 1205, a receiving stem 1210 that extends from the base 1205, and an adhering component 1305 affixed to the base 1205 opposite the receiving stem 1210.

The adhering component 1305 can include an adhesive pad, a threaded hole/slot for screws, a magnet and/or a sucker to affix the mount 1105 to a surface. In other embodiments, the magnet is a polymer magnet (e.g., PAN-iCNQ). The receiving stem 1210 includes an orifice to the receive the arm 1110. In some embodiments, the receiving stem 1210, the arm 1110, the light focusing component 605, or a combination of two or more thereof are a single unit. The mount 1105 can dynamically couple to a surface to facilitate hand-free operation of the otoscope 100. To accomplish this feature, the mount 1105 can include a adhering component 1305. To allow the otoscope 100 to operate in a highly flammable oxygen environment (e.g., greater than 21% PPO2) or a magnetic environment, the adhering component 1305 is preferably a plastic (i.e., polymer) magnet. In some embodiments, the adhering component 1305 includes a sucker to affix the mount 1105 to a surface. To be sure, the otoscope 100 is preferably designed to be completely plastic and non-ferrous.

In other words, the components of the otoscope are each made of polymers and/or non-ferrous materials. As such, the reflective channel 205 includes a non-ferrous surface 510 that is reflective. The reflective lens 305 includes a first non-ferrous surface 505 that is reflective. The light focusing component 605 includes a second non-ferrous surface 705 that is also reflective. For example, the second non-ferrous surface 705 can include a light reflective polymer coating. In some embodiments, the non-ferrous surfaces disclosed herein include polished aluminum. The head 110, the specula 115, and the eye piece 120 are each non-ferrous. Similarly, the fiber optic cable 610, the light focusing component 605, the arm 1110, and the mount 1105 are each non-ferrous. In some embodiments, the arm 1110 is telescopic. In other embodiments, the art 1110 is bendable (e.g., has a radius of curvature of at least 2 inches).

Although the disclosure has been explained in relation to its preferred embodiment, it is to be understood that many other possible modifications and variations can be made without departing from the spirit and scope of the disclosure.

What is claimed is:

1. An otoscope comprising:
    a handle;
    a head coupled to the handle;
    a specula coupled to the head;
    an eye piece coupled to the head opposite the specula;
    a reflective lens positioned within the head;
    a fiber optic cable positioned within the handle;
    wherein
        the handle comprises a first end and a second end positioned opposite the first end;
        the head is coupled to the first end;
        the fiber optic cable provides light to the reflective lens;
        the fiber optic cable extends from the first end to the second end; and
        the reflective lens is oriented to reflect light to the specula.

2. The otoscope of claim 1, further comprising:
    a light focusing component functionally coupled to the fiber optic cable;
    wherein the light focusing component
        is conically shaped;
        comprises an orienting orifice positioned proximate to a channeling orifice;
        captures the ambient light; and
        provides the ambient light to the fiber optic cable.

3. The otoscope of claim 2, further comprising:
    an arm pivotably coupled to the light focusing component;
    a mount coupled to the arm opposite the light focusing component;
    wherein
        the mount comprises:
            a base;
            a receiving stem extending from the base;
            an adhering component affixed to the base opposite the receiving stem; and
            the adhering component comprises a magnet, an adhesive pad, or a sucker.

4. The otoscope of claim 3, wherein
    the reflective lens comprises a first non-ferrous surface;
    the light focusing component comprises a second non-ferrous surface;
    the first non-ferrous surface is reflective; and
    the second non-ferrous surface is reflective.

5. The otoscope of claim 4, wherein
    the head is non-ferrous;
    the specula is non-ferrous; and
    the eye piece is non-ferrous.

6. The otoscope of claim 5, wherein the fiber optic cable is non-ferrous.

7. The otoscope of claim 6, wherein the light focusing component is non-ferrous.

8. The otoscope of claim 7, wherein the arm is non-ferrous.

9. The otoscope of claim 8, wherein the mount is non-ferrous.

10. An otoscope comprising:
    a handle;
    a head coupled to the handle;
    a specula coupled to the head;
    an eye piece coupled to the head opposite the specula;
    a reflective lens positioned within the head;
    a fiber optic cable functionally coupled to the head;
    a light focusing component functionally coupled to the fiber optic cable;
    wherein
        the handle comprises a first end and a second end positioned opposite the first end;
        the head is coupled to the first end;
        the fiber optic cable provides light to the reflective lens;
        the fiber optic cable extends from the first end to the second end;
        the reflective lens is oriented to reflect light to the specula;
        the light focusing component is conically shaped;
        the light focusing component comprises an orienting orifice positioned proximate to a channeling orifice;
        the light focusing component captures ambient light; and
        the light focusing component provides ambient light to the fiber optic cable.

11. The otoscope of claim 10, further comprising:
    an arm pivotably coupled to the light focusing component;
    a mount coupled to the arm opposite the light focusing component;
    wherein the mount comprises:
a base;
a receiving stem extending from the base;
an adhering component affixed to the base opposite the receiving stem; and
the adhering component comprises a magnet, an adhesive pad, or a sucker.

12. The otoscope of claim 11, wherein
the reflective lens comprises a first non-ferrous surface;
the light focusing component comprises a second non-ferrous surface;
the first non-ferrous surface is reflective; and
the second non-ferrous surface is reflective.

13. The otoscope of claim 12, wherein
the head is non-ferrous;
the specula is non-ferrous; and
the eye piece is non-ferrous.

14. The otoscope of claim 13, wherein the fiber optic cable is non-ferrous.

15. The otoscope of claim 14, wherein the light focusing component is non-ferrous.

16. The otoscope of claim 15, wherein the arm is non-ferrous.

17. The otoscope of claim 16, wherein the mount is non-ferrous.

18. An otoscope comprising:
a handle;
a head coupled to the handle;
a specula coupled to the head;
an eye piece coupled to the head opposite the specula;
a reflective lens positioned within the head;
a fiber optic cable functionally coupled to the head;
a light focusing component functionally coupled to the fiber optic cable;
an arm pivotably coupled to the light focusing component;
a mount coupled to the arm opposite the light focusing component;
wherein
the handle comprises a first end and a second end positioned opposite the first end;
the head is coupled to the first end;
the fiber optic cable provides light to the reflective lens;
the fiber optic cable extends from the first end to the second end;
the reflective lens is oriented to reflect light to the specula;
the light focusing component is conically shaped;
the light focusing component comprises an orienting orifice positioned proximate to a channeling orifice;
the light focusing component captures ambient light; and
the light focusing component provides ambient light to the fiber optic cable;
the mount comprises:
a base;
a receiving stem extending from the base;
an adhering component affixed to the base opposite the receiving stem; and
the adhering component comprises a magnet, an adhesive pad, or a sucker.

19. The otoscope of claim 18, wherein
the reflective lens comprises a first non-ferrous surface;
the light focusing component comprises a second non-ferrous surface;
the first non-ferrous surface is reflective; and
the second non-ferrous surface is reflective.

20. The otoscope of claim 19, wherein
the head is non-ferrous;
the specula is non-ferrous;
the eye piece is non-ferrous;
the fiber optic cable is non-ferrous;
the light focusing component is non-ferrous;
the arm is non-ferrous; and
the mount is non-ferrous.

* * * * *